United States Patent [19]

Booth

[11] 4,267,383

[45] May 12, 1981

[54] HYDROCARBONYLATION

[75] Inventor: Frank B. Booth, Anaheim, Calif.

[73] Assignee: Celanese Corporation, New York, N.Y.

[21] Appl. No.: 91,382

[22] Filed: Nov. 5, 1979

Related U.S. Application Data

[60] Continuation of Ser. No. 36,045, May 4, 1979, abandoned, which is a continuation-in-part of Ser. No. 937,653, Aug. 28, 1978, abandoned, Ser. No. 926,046, Jul. 19, 1978, and Ser. No. 886,887, Jan. 4, 1978, abandoned, which is a continuation of Ser. No. 750,770, Aug. 7, 1968, abandoned, said Ser. No. 937,653, is a division of Ser. No. 840,815, Jul. 10, 1969, Pat. No. 4,110,404, which is a continuation-in-part of Ser. No. 518,562, Jan. 4, 1966, abandoned, said Ser. No. 926,046, is a continuation of Ser. No. 464,657, Apr. 26, 1974, abandoned, which is a continuation of Ser. No. 81,502, Oct. 16, 1970, abandoned, which is a continuation of Ser. No. 642,191, May 29, 1967, abandoned.

[51] Int. Cl.³ .............................................. C07C 45/60
[52] U.S. Cl. .................................................... 568/454
[58] Field of Search ................. 260/604 HF; 568/909, 568/451, 454

[56] References Cited

U.S. PATENT DOCUMENTS

| | | | |
|---|---|---|---|
| 2,694,735 | 11/1954 | Hull | 260/604 HF |
| 2,828,344 | 3/1958 | Hughes | 260/604 HF |
| 3,102,899 | 9/1963 | Cannell | 260/604 HF |
| 3,150,188 | 9/1964 | Eisenmann | 260/604 HF |
| 3,167,555 | 1/1965 | Farkas | 260/604 HF |
| 3,168,553 | 2/1965 | Slaugh | 260/604 HF |
| 3,239,566 | 3/1966 | Slaugh | 260/604 HF |
| 3,239,570 | 3/1966 | Slaugh | 260/604 HF |
| 3,278,612 | 10/1966 | Greene | 260/604 HF |
| 3,351,666 | 11/1967 | Mertzweiller | 260/604 HF |
| 3,458,547 | 7/1969 | Stevenson Coffey | 260/604 HF |
| 3,480,659 | 11/1969 | Dewhirst | 260/604 HF |
| 3,487,112 | 12/1969 | Paulik | 260/604 HF |
| 3,488,296 | 1/1970 | Senn | 260/604 HF |
| 3,499,932 | 3/1970 | Pruett | 260/604 HF |
| 3,511,880 | 5/1970 | Booth | 260/604 HF |
| 3,515,757 | 6/1970 | Sibert | 260/604 HF |
| 3,527,809 | 9/1970 | Pruett | 260/604 HF |
| 3,594,425 | 7/1971 | Brader | 260/604 HF |
| 3,933,919 | 1/1976 | Wilkinson | 260/604 HF |
| 3,965,192 | 6/1976 | Booth | 260/604 HF |
| 4,110,404 | 8/1978 | Schaeffer | 260/604 HF |

FOREIGN PATENT DOCUMENTS

| | | | |
|---|---|---|---|
| 1530136 | 6/1968 | France | 260/604 HF |
| 40-22735 | 7/1965 | Japan | 260/604 HF |
| 665705 | 1/1952 | United Kingdom | 260/604 HF |
| 988941 | 4/1965 | United Kingdom | 260/604 HF |

OTHER PUBLICATIONS

Jardine, "Chemistry and Industry", Mar. 27, 1965, p. 560.
Osborn, "Chemical Communications", No. 2/1965, Jan. 27.
Hallman, "Chemical Communications", No. 7/1967, Apr. 12, pp. 305+.
Glasstone, "Textbook of Physical Chemistry", 2nd ed., 1946, NY Nostrand Co., pp. 1044+.

Primary Examiner—Werren B. Lone
Attorney, Agent, or Firm—Kenneth A. Genoni

[57] ABSTRACT

A high yield of straight chain aldehydes, relative to branched chain aldehydes, is obtained by limiting the supply of carbon monoxide to the reaction to a value where the rate of reaction is dependent upon the concentration of carbon monoxide in the homogeneous catalysis of the hydrocarbonylation of hydrocarbon alpha olefins using a catalyst comprising a complex between an organic ligand and a Group VIII noble metal hydride or halide carbonyl. The reaction is performed at mild conditions including temperatures from 50°–200° C. and pressures from 1 to 10,000 atmospheres to produce aldehydes. The aldehydes are useful as intermediates for hydrogenation to aliphatic alcohols, for aldol condensation to produce plasticizers, for oxidation to produce aliphatic acids, etc.

6 Claims, No Drawings

HYDROCARBONYLATION

CROSS-REFERENCE TO RELATED APPLICATIONS

This is a continuation of application Ser. No. 036,045 filed May 4, 1979 entitled "*Hydrocarbonylation*" now abandoned which in turn is a continuation-in-part of my copending application Ser. No. 886,887, filed Jan. 4, 1978, abandoned, which is a continuation of application Ser. No. 750,770, filed Aug. 7, 1968 (now abandoned); Ser. No. 036,045 is also a continuation-in-part of my copending application Ser. No. 937,653, filed Aug. 28, 1978, abandoned, which is a division of application Ser. No. 840,815, filed July 10, 1969 (now patent 4,110,404), which in turn is a continuation-in-part of application Ser. No. 518,562, filed Jan. 4, 1966 (now abandoned); Ser. No. 036,045 is also a continuation-in-part of my copending application Ser. No. 926,046, filed July 19, 1978, which is a continuation of application Ser. No. 464,657, filed Apr. 26, 1974 (now abandoned), which in turn is a continuation of application Ser. No. 81,502, filed Oct. 16, 1970 (now abandoned), which in turn is a continuation of application Ser. No. 642,191, filed May 29, 1967 (now abandoned).

DESCRIPTION OF THE INVENTION

The invention relates to the reductive carbonylation of olefins to aliphatic aldehydes having a high ratio of normal to iso distribution. Hydroformylation of alpha hydrocarbon olefins is used to prepare aldehydes suitable for hydrogenation to alcohols or oxidation to fatty acids. In some instances aldo condensation of the aldehyde product is practiced to obtain high molecular weight products from substantially lower molecular weight olefins, e.g., preparation of 2-ethylhexanol from propylene. In these uses, it is important that the hydroformylation yield a high percentage of normal or straight chain product since the branched chain acids or alcohols are of substantially lesser usefulness. Accordingly, it is important to provide methods of hydroformylation that secure high yields of normal, relative to branched chain, aldehydes.

Recent advances in catalysis have developed hydroformylation using ligand complexes of Group VIII noble metals. These processes exhibit activity at considerably less severe operating conditions, e.g., lower pressures and temperatures than the previously used catalysts. In addition, the ligand imparts greater stability to the homogeneous catalyst than possessed by prior catalysts.

Some of these advances are disclosed in applications, Ser. Nos. 518,562, filed Jan. 4, 1966 (now abandoned); 840,815, filed July 10, 1969 (now U.S. Pat. No. 4,110,404); 937,653, filed Aug. 28, 1978; and 579,825, filed Sept. 16, 1966 (now U.S. Pat. No. 3,511,880), wherein it is disclosed that the activity of these noble metal halide catalysts can be enhanced by the inclusion of cocatalysts in the liquid phase such as heterocyclic bridgehead amines or strongly basic materials; and Ser. Nos. 642,191, filed May 29, 1967 (now abandoned); 81,502,1974 (now abandoned); and 926,046, filed July 19, 1978, which disclose the use of noble metal hydride-ligand complex catalysts for hydroformylation.

I have now found that the higher than expected yields of the normal or straight chain aldehydes can be achieved by use of limited amounts of carbon monoxide during hydroformylations with a hydride or halide of a Group VIII noble metal carbonyl catalyst which is complexed with an organic ligand selected from the class consisting of organic phosphines, phosphites, arsines and stibines. When the supply of carbon monoxide to the reaction is limited past the point where further limitation causes a decrease in reaction rate, surprisingly, it was found that the yield of normal or straight chain aldehyde relative to the branched chain aldehyde is significantly increased. When the catalyst is employed as a hydride, a high activity is observed in the absence of any cocatalyst. When the catalyst is used as a halide, it is preferred to include in the solution a cocatalyst which is a bridgehead nitrogen heterocycloamine and which significantly increases the rate of reaction with the halide catalyst.

The catalyst used in the invention comprises a complex combination of a Group VIII noble metal hydride or halide with carbon monoxide and an organic ligand. The Group VIII noble metal can be of the palladium subgroup, i.e., palladium, rhodium or ruthenium, or of the platinum subgroup, i.e., platinum, osmium or iridium. The catalyst if employed in its hydride form can be prepared by treatment of the metal salt with a strong reducing agent as set forth hereinafter. The metal hydride or halide carbonyl is in association with a biphyllic ligand which is an organic material having one atom selected from the group of phosphorus, arsenic, antimony and bismuth in the trivalent state and having an unshared pair of electrons capable of coordinate covalent bonding with the catalyst to thereby form a complex useful in the catalysis.

With the aforementioned catalyst, described in greater detail hereinafter, the carbonylation of ethylenically unsaturated compounds proceeds rapidly at relatively mild conditions including temperatures from about 0° to about 250° C. and pressures of from 1 to about 1000 atmospheres with hydrogen and, as hereinafter described, limited amounts of carbon monoxide.

The ethylenically unsaturated compound carbonylated in accordance with my invention can comprise any hydrocarbon alpha olefin having from 2 to about 25 carbons; preferably from 2 to about 18 carbons. This olefin has the following structure:

$$R_2R_1C=CH_2$$

wherein $R_1$ and $R_2$ are hydrogen, alkyl, cycloalkyl, aryl, alkaryl or aralkyl.

Examples of useful olefins are the hydrocarbon olefins such as ethylene, propylene, butene-1, 2-methylbutene-1, hexene-1, 3-ethylhexene-1, isobutylene, octene-1, 2-propylhexene-1, ethyl-cyclohexene, decene-1, 4,4'-dimethylnonene-1, dodecene-1, undecene-1, 6-propyldecene-1, tetradecene-1, 7-amyldecene-1, hexadecene-1, 4-ethyltridecene-1, octadecene-1, 5,5-dipropyldodecene-1, vinylcyclohexane, allylcyclohexane, styrene, p-methylstyrene, alpha-methylstyrene, p-vinylcumene, betavinylnaphthalene, 1,1-diphenylethylene, allylbenzene, 6-phenylhexene-1, 1,3-diphenylbutene-1, 3-benzylheptene-1, o-vinyl-p-xylene, m-methylstyrene, divinylbenzene, 1-allyl-4-vinylbenzene, p-ethylstyrene, etc. Of the preceding, the alpha olefins having 2 to about 16 carbons are preferred classes.

The reaction is performed under liquid phase conditions and, when the olefin comprises a liquid at the reaction conditions, the olefin can be used in excess to provide the liquid reaction medium. If desired, however, any suitable organic liquid can be employed as a reaction solvent; preferably, organic solvents which are inert to the reaction conditions, the reactants, the catalyst and the products are employed. Examples of suitable solvents which can be used in accordance with my invention include hydrocarbons such as the aromatic, aliphatic or alicyclic hydrocarbons, ethers, esters, ketones, etc.

Examples of suitable hydrocarbons that can be employed in the solvents include aromatic hydrocarbons such as benzene, toluene, xylene, ethylbenzene, tetralin, etc.; aliphatic hydrocarbons such as butane, pentane, isopentane, hexane, isohexane, heptane, octane, isooctane, naphtha, gasoline, kerosene, mineral oil, etc.; alicyclic hydrocarbons, e.g., cyclopentane, cyclohexane, methylcyclopentane, decalin, indane, etc.

Various alkyl and aryl ketones can also be employed as the reaction solvent, e.g., acetone, methylethyl ketone, diethyl ketone, diisopropyl ketone, ethyl-n-butyl ketone, methyl-n-amyl ketone, cyclohexanone, diisobutyl ketone, etc.

Ethers can also be employed as the reaction solvent, e.g., diisopropyl ether, di-n-butyl ether, ethylene glycol diisobutyl ether, methyl o-tolyl ether, ethylene glycol dibutyl ether, diisoamyl ether, methyl p-tolyl ether, methyl m-tolyl ether, dichloroethyl ether, ethylene glycol diisoamyl ether, diethylene glycol diethyl ether, ethylbenzyl ether, diethylene glycol diethyl ether, diethylene glycol dimethyl ether, ethylene glycol dibutyl ether, ethylene glycol diphenyl ether, triethylene glycol diethyl ether, diethylene glycol di-n-hexyl ether, tetraethylene glycol dimethyl ether, tetraethylene glycol dibutyl ether, etc.

Various esters can also be employed as the solvent, e.g., ethyl formate, methyl acetate, ethyl acetate, n-propyl formate, isopropyl acetate, ethyl propionate, n-propyl acetate, sec-butyl acetate, isobutyl acetate, ethyl n-butyrate, n-butyl acetate, isoamyl acetate, n-amyl acetate, ethyl formate, ethylene glycol diacetate, glycol diformate, cyclohexyl acetate, furfuryl acetate, isoamyl n-butyrate, diethyl oxalate, isoamyl isovalerate, methyl benzoate, diethyl malenate, valerolactone, ethyl benzoate, methyl salicylate, n-propyl benzoate, n-dibutyl oxalate, n-butyl benzoate, diisoamyl phthalate, dimethyl phthalate, diethyl phthalate, benzyl benzoate, n-dibutyl phthalate, etc. A preferred class of ester solvents includes the lactones, e.g., butyrolacetone, valerolactone and their derivatives having lower ($C_1$–$C_5$) alkyl substituents.

Alcohols can also be employed as a reaction solvent. Preferably tertiary alcohols are employed since these materials are substantially non-reactive under the reaction conditions. Primary and secondary alcohols can be employed but are less preferred since these materials can react with aldehyde compounds under the reaction conditions to produce acetals. While in some instances these may be desired products, it is generally desirable to produce the carbonyl compound or alcohol directly without the formation of the acetal. It is of course apparent, if desired, that the acetal can be hydrolyzed to obtain the aldehyde. Examples of alcohols that can be employed as solvents include the aliphatic and alicyclic alcohols such as methanol, ethanol, isopropanol, butanol, t-butanol, t-amyl alcohol, hexanol cyclohexanol, etc.

Ligand

The catalyst comprises a Group VIII noble metal hydride or halide in complex association with carbon monoxide and an organic phosphite, phosphine, arsine, stibine or bismuthine. The trivalent phosphorus, arsenic, antimony or bismuth atom has a pair of electrons capable of forming a coordinate covalent bond with the metal atom and simultaneously has the ability to accept the electron from the metal, thereby imparting additional stability to the resulting complex. Biphyllic ligands can comprise organic compounds having at least about 3 carbons and containing arsenic, antimony, phosphorus or bismuth in a trivalent state. Of these, the phosphines are preferred; however, phosphites, arsines, stibines and bismuthines can also be employed. In general, these biphyllic ligands have the following formula:

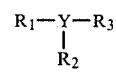

wherein:
Y is As, Sb, P, Bi or P—O)$_3$;
$R_1$ and $R_2$ are hydrogen, alkyl from 1 to about 8 carbons or aryl from 6 to about 9 carbons, or amino, alkoxy or halo substitution products thereof; and
$R_3$ is alkyl from 1 to 8 carbons, aryl from 6 to 9 carbons or

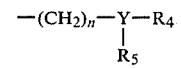

wherein:
n is from 3 to about 6; and
$R_4$ and $R_5$ are alkyl from 1 to about 8 carbons or aryl from 6 to about 9 carbons.

Examples of suitable biphyllic ligands useful in my invention to stabilize the catalyst composition are the following: trimethylphosphine, trimethylphosphite, triethylarsine, triethylbismuthine, triisopropylstibine, chlorodiethylphosphine, chlorodipropylarsine, tri(aminobutyl)arsine, tris(aminoamyl)phosphine, ethyldiisopropylstibine, tricyclohexylphosphine, tri(aminocyclohexyl)stibine, triphenylphosphine, triphenylphosphite, triphenylbismuthine, tris (N,N-dimethylanilyl)-phosphine, tris(o-tolyl)phosphine, triphenylbismuthine, tris(2-ethylhexyl)arsine, tris(methylcyclopentyl)stibine, tris(cholorophenyl)bismuthine, trianilylbismuthine, phenyldiisopropylphosphine, phenyldiamylphosphine, ethyldiphenylphosphine, chlorodixylylphosphine, chlorodiphenylphosphite, tris(N,N-diethylaminoethyl)phosphine, ethylene bis(diphenylphosphine), tritolylphosphine, tricyclohexylphosphite, tris(methylcyclopentyl)arsine, tritolylstibine, hexamethylene bis(diisopropylarsine), pentamethylene bis(diethylstibine), diphenyl(N,N-dimethylanilinyl)phosphine, triphenylanilylethylenediphosphine, trianilinylphosphine, tris(3,5-diaminophenyl)phosphine, trianilinylarsine, anilinyldiphenylbismuthine, aminoethyltriisopropylhexamthylenediphosphine, chlorophenyltriphenylpentamethylenediarsine, tetraethylethylenedibismuthine, tetraphenylethylenediphosphite, tetramethyltrimethylenedistibine, etc. Of the aforementioned, the aryl phosphines are preferred with Group VIII noble metals because of the demonstrated greater activity of noble metal catalysts comprising the aryl phosphines.

Preparation Of The Hydride Catalyst

The Group VIII noble metal hydride complexes with carbon monoxide and the ligand can be formed by reduction of a metal salt carbonyl-ligand complex or can be formed from the metal hydrides themselves. Examples of suitable sources of the noble metals are as follows: bis(triphenylphosphine)iridium carbonyl chloride; tris(triphenylphosphine)iridium carbonyl hydride; iridium carbonyl; iridium tetrabromide, iridium tribromide, iridium triflouride; iridium trichloride; osmium trichloride; chloroosmic acid; palladium hydride; palladous chloride, palladous cyanide; palladous iodide; palladous nitrate, platanic acid; platanous iodide; palladium cyanide; sodium hexachloroplatinate; potassium trichloro(ethylene)platinate(II); chloropentaaminorhodium(III) chloride; rhodium dicarbonyl chloride dimer; rhodium nitrate; rhodium trichloride; tris(triphenylphosphine)rhodium carbonyl hydride; tris(triphenylphosphine)rhodium(I)chloride; ruthenium trichloride; tetraaminorutheniumhydroxychloro chloride, etc.

Of the aforementioned, the hydride carbonyl complexes with triphenylphosphine of rhodium and iridium can of course be directly added to the reaction as the catalytically active material. The hydride carbonyls can also be formed from the hydrides such as palladium hydride by adding the palladium hydride and excess of the organic ligand to a reaction zone containing an inert liquid and introducing carbon monoxide into the liquid phase to form the carbonyl. Atmospheric or superatmospheric pressures up to about 1000 atmospheres can be used as desired to accelerate the formation of the carbonyl complex catalyst.

The hydride catalyst can also be formed from the Group VIII noble metal salts previously mentioned. In this preparation the Group VIII noble metal salt is subjected to a reduction with a strong reducing agent and this reduction can be performed in the presence of either or both of the carbon monoxide and ligand. When only one of these components is present during the reduction, the remaining component can be added after the reduction to form the cataylst complex. Suitable strong reducing agents comprises the alkali metal hydrides and the alkali metal boron and aluminum hydrides such as sodium hydride, potassium hydride, lithium hydride, boron hydride, e.g., sodium borohydride, potassium borohydride, lithium borohydride, cesium borohydride, sodium aluminum hydride, lithium aluminum hydride, potassium aluminum hydride, cesium aluminum hydride, etc., in a suitable inert organic solvent such as any of those aforementioned. When nonhalide sources are used such as the nitrate or sulfate, salts are used, reduction to the hydride can be achieved by treatment with hydrazine using any inert organic solvent such as those aforementioned. The reduction is performed at relatively mild temperatures from about 25° to about 75° C. and, preferably, is performed in aqueous alkanol solvent. The reduction results in the reduction of the metal salt, e.g., rhodium nitrate to rhodium hydride. When this reaction is performed in the presence of the organic ligand and under carbon monoxide pressure, the Group VIII noble metal hydride complex with carbon monoxide and triphenylphosphite can be obtained directly.

Preparation Of The Halide Catalyst

The halide containing complex catalyst can be formed by contacting a halide salt of the noble metal with the ligand and a suitable source of carbon monoxide such as carbon monoxide or an aliphatic amide, e.g., formamide, dimethyl formamide, acetamide, etc. The catalyst can be formed by contacting the noble metal halide, e.g., ruthenium trichloride, rhodium trichloride, iridium trifluoride, osmium dibromide, platinum diiodide, palladium dichloride with the phosphite and then introducing carbon monoxide and, if desired, hydrogen. The contacting can be performed in aqueous solvents or in any of the organic liquids previously described as suitable hydroformylation solvents. The contacting of the catalyst components can be performed at temperatures from about 25° to 225° C. and at pressures from 1 to about 1000 atmospheres. A suitable preparation comprises refluxing the solution containing the components under a carbon monoxide atmosphere at 1 to about 10 atmospheres pressure.

The catalyst can be formed directly in the reaction zone prior to introducing the olefin and commencing the hydro-carbonylation or it can be purified by crystallization from the liquid media used in its preparation and introduced as a preformed complex.

The noble metal complex is employed in the reaction zone in catalytic amounts and this is generally an amount sufficient to provide a concentration of the Group VIII noble metal between about 0.002 and about 2.0 weight percent of the liquid reaction medium and preferably between about 0.05 and about 0.5 weight percent.

The cocatalyst employed with the aforementioned Group VIII noble metal halide carbonyl organic liqand complex is a poly(heterocyclo)amine having at least one nitrogen in a bridgehead position. The term "bridgehead position" is well established in chemcial nomenclature to identify the position of an atom which is common to at least two of the rings of the polycyclo compound. Preferably the amine is a atom-bridged system, i.e., atoms, generally methylene carbons, form the bridge or link in the molecule rather than a simple valence bonding. The amine is also used in catalytic amounts, e.g., from about 0.001 to about 10 weight percent; preferably from about 0.05 to 5 weight percent of the liquid reactio medium. In general, amines having from 1 to about 4 nitrogen atoms and from 1 to about 25 carbons; preferably from 2 to about 10 carbons; can be employed for this purpose and the following is a listing of representative amines useful in my invention: 1,2,4-triazabicyclo(1.1.1) pentane; 1,5,6-triazabicyclo(2.1.1) hexane; 5-oxa-1,6-diazabicyclo(2.1.1)hexane; 5-thia-1,6-diazabicyclo(2.1.1)hexane; 2-oxa-1,5,6-triazabicyclo(2.1.1)hexane; 1,2,5,6-tetrazabicyclo(2.1.1)hexane; 5-oxa-1,2,3,6-tetrazabicyclo (2.1.1)hexane; 1-azabicyclo(3.3.1)heptane; 1-azabicyclo(2.2.1) heptane; 1,4-methano-1,1-pyridine; 2-ox-1-azabicyclo(2.2.1)heptane; 1,4-diazabicyclo(2.2.1)heptane; 7-oxa-1-azabicyclo(2.2.1)heptane; 7-thia-1-azabicyclo(2.2.1)heptane; 1,7-diazabicyclo(2.2.1) heptane; 1,3,5-triazabicyclo(2.2.1)heptane; 1-azabicyclo(3.2.1) octane; 1,5-diazatricyclo(4.2.1)decane; 1,7-diazatricyclo(3.3.1.2)undecane; 7ox-1-azabicyclo(3.2.1)octane; 1,7-diazabicyclo(3.2.1)octane; 3-thia-1,7-diazabicyclo(3.2.1)octane; 1,3,6,8-tetrazatricyclo(6.2.1.1)dodecane; 2,8-diazatricyclo (7.3.1.1)tetradecane; 1-azabicyclo(3.3.1)nonene, also known as 1-isogranatinine and the oxo, hydroxy and lower alkyl derivatives thereof; 1-azabicyclo(2.2.2)octane also known as quinuclidine as well as the halo, oxo, hydroxy and lower alkyl derivatives thereof; 1-azatricyclo(3.3.1.1)decane; 1,3-diazabicyclo(2.2.2)octane; 1,3-diazabicyclo(3.3.1)nonene; 1,6-diazatricyclo(5.3.1)dodecane; 2-ox-1-azabicyclo(2.2.2)octane; 4,6,10-triox-1-azatricyclo(3.3.1.1)decane; 1,5-diazabicyclo(3.3.1)nonene; 1,2,5,8tetrazatricyclo(5.3.1.1)dodecane; 1,4-diazabicyclo(2.2.2)octane also known as triethylene diamine and its oxo, hydroxy, halo and lower alkyl derivatives thereof; 1,3-diazatricyclo(3.3.1.1) decane also known as 1,3-diazaadamantane; 1,3,5-triazatricyclo(3.3.1)decane; 1,3,5,7-tetrazabicyclo(3.3.1)nonene also known as pentamethylene tetramine; 1,3,5,7-tetrazatricyclo(3.3.1.1) decane also known as hexamethylene tetramine; 2-oxa-1,3,4-triazabicyclo(3.3.1)nonene; 1-azabicyclo(4.3.1)decane; 1-azabicyclo(3.2.2)nonene; 1,5-diazabicyclo(3.2.2)nonene; 1,3,5,7-tetrazabicyclo(3.3.2)decane; 1,5-diazabicyclo(3.3.3)undecane; etc.

The reaction is performed under relatively mild conditions including temperatures from about 50° to about 200° C.; preferably from about 70° to about 150° C. Sufficient pressure is used to maintain the reaction medium in liquid phase. Although atmospheric pressure can be used, the rate of reaction is increased by superatmospheric pressures and, therefore, pressures from about 5 to about 300 atmospheres and preferably from about 10 to about 100 atmospheres are used. The preceding conditions are maintained by conventional means. Since the reaction is exothermic, the temperature can be maintained by suitable cooling of all or a portion of the reaction zone contents. The pressure can be maintained by the pressure of the gases supplied to the reaction zone. If desired, a suitable inert gas can also be charged to the reaction zone to reduce the partial pressures of the reacted gases, i.e., hydrogen and carbon monoxide. Nitrogen is a suitable inert gas.

The relative concentration of the carbon monoxide and hydrogen significantly affects the distribution of the normal and branched chain insomers in the product. The carbon monoxide to hydrogen ratio can be maintained from about 1:10 to about 1:3 and preferably from about 1:10 to about 1:5 to favor production of the straight chain aldehyde. Surprisingly, under these high hydrogen partial pressures, the straight chain product can be obtained in amounts from 3 to 8 times the yield of the branched chain aldehyde.

The reaction when performed under conditions that insure adequate mass transfer and diffusion of reactants is generally independent of the rate of supply of carbon monoxide in ratios of hydrogen to carbon monoxide from 1:10 to about 10:1. Thus when the reactant gases are sparged into the liquid phase and this liquid phase is adequately agitated, e.g., by stirring the reaction rate constant, K, is independent of carbon monoxide partial pressure and is first order dependent on the concentrations of catalyst, olefin and hydrogen. When less adequate mixing techniques are employed, e.g., when the liquid phase is not stirred and/or is not sparged with the reactant gases the reaction rate can become dependent on the carbon monoxide concentration at ratios of hydrogen to carbon monoxide as low as about 3:1.

When the carbon monoxide supply to the hydroformylation is limited to a level where the reaction rate is responsive to the carbon monoxide concentration, e.g., the partial pressure of carbon monoxide in the reactor gas phase, I have found that a significant increases in the yield of the normal, relative to the branded chain, aldehyde occurs. This increase can conveniently be expressed as an increase in the ratio of the normal to isoaldehyde (n/i).

The invention therefore comprises performing the aforedescribed hydroformylation process while maintaining the concentration of hydrogen to carbon monoxide between about 3:1 and about 250:1 and sufficient to cause the reaction rate to become dependent on this relative concentration. Since the concentrations of these gaseous reactants are proportional to their partial pressures in the gas phase of the reactor, the concentrations can be simply maintained by controlling the supply of these reactants so as to maintain their partial pressures within the aforementioned ratios. Preferred ratio ranges depend somewhat on mixing techniques; e.g., sparged and stirred reactors requre high values for the ratio from about 35:1 to about 200:1 sparged and unstirred reactors from 12:1 to about 100:1; stirred and unsparged reactors from 3:1 to about 20:1.

The selectivity of the reaction for a straight chain aldehyde can also be increased by including limited amounts of water in the reaction zone. While the practice of the invention under substantially anhydrous conditions with about equal molar quantities of carbon monoxide and hydrogen is preferred, the addition of water to this reaction in amounts from 1 to about 50 percent of the liquid reactants can also significantly increase the yield of normal aldehyde. The aforementioned increase in hydrogen concentration, relative to carbon monoxide, can also be performed in the partially aqueous solvent to obtain even greater yields of the straight chain product. A typical embodiment uses water from 5 to about 15 weight percent of the liquid reactants.

The process can be conducted continuously or batchwise; however, the continuous processing is preferred. In the latter preferred technique, the catalyst is charged to the reaction zone in a suitable solvent or in excess of the olefin and the gaseous reactants are introduced into contact with the reaction solent and catalyst in the reaction zone. A continuous withdrawal of the liquid phase in the reaction zone can be employed; this material is then reduced in pressure to remove the dissolved gases which can be recycled, cooled and then distilled to recover the desired products. When low molecular weight products are produced, e.g., propionaldehyde, this product can be recovered by employing a high gas rate through the reactor to strip the product from the reaction solent which, desirably, is a higher boiling liquid such as tertiary butanol, tertiary amyl alcohol, butyrolactone, etc.

Because the reaction conditions are very mild, the products can remain in the reaction zone without encountering undue degradation to less desired products and therefore batchwise operation can be practiced by introducing the olefin, hydrogen and carbon monoxide into contact with the catalyst solution until a sufficient inventory of product is accumulated in the reaction zone and thereafter the reaction discontinued and the product recovered by suitable steps, typically distillation.

A preferred embodiment of the invention utilizes excess of the organic ligand. Use of excess amounts as hereafter defined has been found to increase the rate of reaction and to increase the yield of the normal, i.e., straight chain, carbonyl product. Excess quantities of the ligand include from 2 to about 100 times the stoichiometric amount of ligand that is complexed with the noble metal catalyst. Preferably, the amount in excess is from 5 to about 20 times this stoichiometric quantity. The stoichiometric quantity varies between the noble metals but is from 2 to about 4 and usually 3 molar quantities of ligand per atomic quantity of noble metal.

The practice of the invention will now be illustrated by the following examples which will also serve to demonstrate the results obtainable thereby:

EXAMPLE 1

The hydroformylation of proplyene is performed in a half-gallon titanium autoclave having a stirrer and means to introduce the reactants into the liquid contents of the autoclave. In a series of experiments, the autoclave is charged with 0.3 gram rhodium trichloride, 2.0 grams 1,4-diazabicyclo- (2.2.2)octane, 2.0 grams triphenylphosphine and 250 milliliters butyrolactone. The autoclave is closed, pressured with carbon monoxide, then with hydrogen to provide a total pressure of 600 psig, and heated to and maintained at 190° F. for the periods indicated in the following table. The autoclave was depressured, collecting the condensible gases and the condensate and autoclave contents analyzed. The following table summarizes the results:

| Experiment | Time, Minutes | H/CO | Aldehyde Grams | n/i | Condensible Gas $C_3H_8$ | $C_3H_6$ |
|---|---|---|---|---|---|---|
| 1 | 25 | 1/1 | 93 | 2.15 | 0.17 | 31.8 |
| 2 | 15 | 3/1 | 53 | 3.7 | — | — |
| 3 | 20 | 5/1 | 10 | 8.0 | 7.16 | 55.3 |

The preceding data evidence that a very significant increase in yield of normal aldehyde can be obtained by limiting the carbon monoxide supply to a level where the reaction rate is decreased by such limitation.

The experiments 1 and 3 are repeated with inclusion of 10 weight percent water in the solvent and the following results are obtained:

| Experiment | Time, Minutes | H/CO | Aldehyde Grams | n/i | Condensible Gas $C_3H_8$ | $C_3H_6$ |
|---|---|---|---|---|---|---|
| 4 | 6 | 1/1 | 96 | 3.6 | 9.3 | 46.6 |
| 5 | 14 | 5/1 | 21 | 9.2 | 40.54 | 38.53 |

EXAMPLE 2

The hydroformylation of proplyene is performed in a continuous bench scale reactor comprising a titanium tube 2½ inches in diameter having a stirring paddle 1⅜ inches in diameter by 9/16 inch wide centrally positioned near the bottom of the reactor and surrounded by a baffle 2⅜ inches in diameter. A helical coil connected to a supply of cooling water is placed in the reactor. A gas introduction tube connected to a source of hydrogen and carbon monoxide enters the reactor and terminates at a point about 9½ inches above the reactor bottom.

The reactor is charged with sufficient of the liquid reaction medium to raise the liquid level to adjacent the end of the gas introduction tube so that the experiments are performed in a stirred but unsparged system. The reaction medium comprises 0.6 gram tris(triphenylphosphine)rhodium carbonyl hydride and 5 grams triphenylphosphine per liter of a 2:1 mixture of normal and iso-butyraldehydes. A gaseous effluent is continuously withdrawn from the reactor, cooled, and the butyraldehyde product condensed therefrom and the uncondensed vapors are admixed with a fresh supply of hydrogen, cabon monoxide and propylene and returned to the reactor through the gas inlet line. Sufficient solvent is added to the reactor, when necessary, through a separate introduction line.

In a series of experiments, the reactor is stirred at 1200 rpm and the temperature of the reactants is maintained at 200° F., and the total reactor pressure is at 500 psig while propylene is continuously introduced at a constant rate between about 0.5 and 0.8 pounds per hour. The carbon monoxide and hydrogen are supplied at varied rates to maintain the partial pressures of these components set forth in the following table which summarizes the results:

| Experiment | Partial Pressure | | | | Aldehyde | | Reaction Rate Constant, K |
|---|---|---|---|---|---|---|---|
| | $C_3H_6$ | CO | $H_2$ | $H_2/CO$ | Grams/hr | n/i | |
| 6 | 57 | 197 | 267 | 1.4 | 249 | 2.1 | 20 |
| 7 | 52 | 116 | 335 | 2.9 | 225 | 2.3 | 15.9 |
| 8 | 51 | 107 | 340 | 3.2 | 234 | 2.5 | 16.7 |
| 9 | 52 | 79 | 368 | 4.7 | 286 | 2.5 | 18.4 |
| 10 | 66 | 52 | 382 | 7.4 | 316 | 3.1 | 15 |
| 11 | 48 | 30 | 417 | 14.0 | 139 | 4.2 | 8.5 |
| 12 | 55 | 16 | 434 | 27.6 | 80 | 6.5 | 4.1 |

These data evidence that as the $H_2/CO$ ratio is increased above about 4.7:1 for a stirred and unsparged system, the reaction rate (K) decreases and the yield of normal or straight chain aldehyde increases.

In related experiments the rate of stirring is altered and the following results are obtained:

| Experiment | Stirrer rpm | Partial Pressure | | | | Aldehyde | | Reaction Rate Constant, K |
|---|---|---|---|---|---|---|---|---|
| | | $C_3H_6$ | CO | $H_2$ | $H_2/CO$ | Gm/Hr. | n/i | |
| 13 | 600 | 56 | 113 | 335 | 3.0 | 183 | 2.8 | 11.9 |
| 14 | 300 | 103 | 127 | 279 | 2.2 | 68 | 2.4 | 2.9 |

The preceding data demonstrate that the reaction rate and yield of normal aldehyde are dependent on the agitation applied to the liquid phase.

EXAMPLE 3

The reactor gas inlet is altered to provide a gas distributor at the bottom of the reactor, beneath the stirrer to which the gas inlet is connected, thereby providing a stirred and sparged system. In a series of experiments the reactor contents are maintained at 200° F., the pressure at 825 psig, the stirrer at 1200 rpm, the catalyst concentration at 179 milligrams rhodium per liter of solvent and the hydrogen and carbon monoxide supplies are varied to obtain the following results:

| Experiment | Partial Pressure | | | | Aldehyde | | Reaction Rate Constant, K |
|---|---|---|---|---|---|---|---|
| | $C_3H_6$ | CO | $H_2$ | $H_2/CO$ | Grams/hr | n/i | |
| 15 | 53 | 177 | 286 | 1.6 | 332 | 2.03 | 23.6 |
| 16 | 51 | 103 | 362 | 3.5 | 332 | 2.09 | 23.4 |
| 17 | 57 | 119 | 637 | 5.4 | 489 | 2.07 | 17.5 |
| 18 | 45 | 97 | 669 | 6.9 | 537 | 2.12 | 22.9 |
| 19 | 49 | 17 | 746 | 43 | 481 | 2.36 | 16.9 |

EXAMPLE 4

The following series of experiments illustrate the effect of varied carbon monoxide/hydrogen ratios of the product distribution. The one-half gallon autoclave was charged with 250 grams butyrolactone, 2 grams 1,4-diazabicyclo(2.2.2)octane, 2 grams triphenylphosphine, 0.3 gram rhodium chloride. The autoclave was closed, purged with nitrogen and 132 grams propylene were introduced. Carbon monoxide was then introduced to raise the autoclave pressure by 300 psi and then an additional 300 psig increase with hydrogen. The autoclave was heated to 195°–250° F. and maintained at that temperature for 8 minutes. The autoclave was then cooled, depressured and opened and the liquid contents distilled to recover 104 grams of mixed butyraldehydes having a ratio of the normal to the isomer of 2.5.

The experiment was repeated; however, the autoclave was pressured with only 150 psi of carbon monoxide and 450 psi (total pressure about 725 psig) with hydrogen. After 15 minutes at 190° F. the autoclave was cooled and the contents distilled to recover 53 grams mixed butyraldehydes having a ratio of the normal to the isomer of 3.7.

The experiment was again repeated; however, the autoclave was pressured only 100 psig with carbon monoxide and 500 psi (total pressure about 725 psig) with hydrogen. A total of 17 grams mixed butyraldehydes was obtained within a 20-minute reaction period at 185°–190° F. with a ratio of the normal to the branched chain aldehyde of 8.0.

EXAMPLE 5

The following experiments illustrate the effect of water on the reaction rate and product distribution. Into a one-half gallon autoclave was charged 300 grams butyrolactone, 50 grams water, 2 grams 1,4-diazabicyclo(2.2.2)octane, 2 grams triphenylphosphine and 0.4 gram rhodium chloride. The autoclave was closed, purged with nitrogen and 104 grams of propylene were introduced. Thereafter equal volumes of carbon monoxide followed by hydrogen were introduced to raise the pressure 600 psi. The autoclave was heated to 190° F. and maintained at that temperature for 6 minutes, then cooled, depressured and opened. The liquid products were distilled to obtain 90.5 grams normal butyraldehyde and 21.7 grams isobutyraldehyde (ratio of 4.17).

The experiment was repeated; however, the water content was increased to 87 grams and the butyrolactone content was decreased to 263 grams. The following products were obtained within a 6 minute reaction period at 190° F.: 96.3 grams normal butyraldehyde and 20.4 grams isobutyraldehyde (ratio of normal to iso of 4.23).

The experiment was repeated substituting 35 grams water and 315 grams butyrolactone for the previously employed solvent. The following products were obtained within a 6 minute reaction period at 190° F.: 90.0 grams normal butyraldehyde and 25.1 grams isobutyraldehyde (ratio of normal to iso of 3.6 ).

While the preceding illustrates hydroformylation with rhodium catalyst, substantially the same results—although at lower reaction rates—can be obtained with the direct substitution of an equivalent weight of the other noble metal complexes, e.g., tris(triphenylphosphine)iridium hydride carbonyl or bis(tritolylphosphite)ruthenium carbonyl chloride for the rhodium catalysts described in the illustrations.

While the preceding examples describe a preferred mode of practice of the invention, it is not intended that the invention be unduly limited by the exemplified disclosure but instead that the invention be defined by the steps and reagents, and their obvious equivalents, set forth in the following claims:

I claim:

1. In a process for hydroformylating hydrocarbon alpha olefins having from 3 to about 25 carbon atoms to form aldehydes, wherein the process is carried out in a reaction zone: (1) in the presence of a liquid reaction medium, (2) with carbon monoxide and hydrogen, (3) at a temperature of about 50° to about 200° C., (4) at a pressure of about 1 to about 10,000 atmospheres, and (5) with a catalyst comprising a complex between a rhodium carbonyl hydride or a rhodium carbonyl halide and an organic ligand of the formula:

$$R_1 - P - R_2 \atop | \atop R_3$$

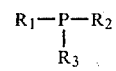

wherein $R_1$, $R_2$ and $R_3$ are aryl of 6 to about 9 carbon atoms, the improvement comprising:
sparging said carbon monoxide and hydrogen into said liquid reaction medium and maintaining in said reaction zone a relative concentration of hydrogen to carbon monoxide of at least 12/1, thereby effecting an increase in the yield of straight chain, relative to branched chain, aldehyde product.

2. The process of claim 1 wherein the liquid reaction medium is stirred and the relative concentration of hydrogen to carbon monoxide is maintained at a value greater than about 35:1.

3. In a continuous process for hydroformylating hydrocarbon alpha olefins having from 3 to about 25 carbon atoms to form aldehydes, wherein the process is carried out in a reaction zone: (1) in the presence of a liquid reaction medium, (2) with carbon monoxide and hydrogen, (3) at a temperature of about 50° to about 200° C., (4) at a pressure of about 1 to about 10,000 atmospheres, and (5) with a catalyst comprising a complex between a rhodium carbonyl hydride or a rhodium carbonyl halide and an organic ligand of the formula:

$$R_1 - P - R_2 \atop | \atop R_3$$

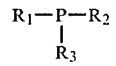

wherein $R_1$, $R_2$ and $R_3$ are aryl of 6 to about 9 carbon atoms;

wherein liquid reaction medium is continuously withdrawn from the reaction zone; wherein dissolved reactant gases are removed from the withdrawn liquid reaction medium; and wherein the reactant gases, removed from the withdrawn liquid reaction medium, are recycled to the reaction zone; the improvement comprising:
sparging said carbon monoxide and hydrogen into said liquid reaction medium and maintaining in said reaction zone a relative concentration of hydrogen to carbon monoxide of at least 12/1, thereby effecting an increase in the yield of straight chain, relative to branched chain, aldehyde product.

4. The process of claim 3 wherein the liquid reaction medium is stirred and the relative concentration of hydrogen to carbon monoxide is maintained at a value greater than about 35:1.

5. In a continuous process for hydroformylating hydrocarbon alpha olefins having from 3 to about 25 carbon atoms to form aldehydes, wherein the process is carried out in a reaction zone: (1) in the presence of a liquid reaction medium, (2) with carbon monoxide and hydrogen, (3) at a temperature of about 50° to about 200° C., (4) at a pressure of about 1 to about 10,000 atmospheres, and (5) with a catalyst comprising a complex between a rhodium carbonyl hydride or a rhodium carbonyl halide and an organic ligand of the formula:

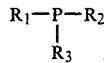

wherein $R_1$, $R_2$ and $R_3$ are aryl of 6 to about 9 carbon atoms;

wherein a gaseous effluent is continuously withdrawn from the reaction zone; wherein the gaseous effluent is cooled to condense the aldehydes formed; and wherein the uncondensed vapors are recycled to the reaction zone; the improvement comprising:

sparging said carbon monoxide and hydrogen into said liquid reaction medium and maintaining in said reaction zone a relative concentration of hydrogen to carbon monoxide of at least 12/1, thereby effecting an increase in the yield of straight chain, relative to branched chain, aldehyde product.

6. The process of claim 5 wherein the liquid reaction medium is stirred and the relative concentration of hydrogen to carbon monoxide is maintained at a value greater than about 35:1.